US010550428B2

(12) United States Patent
Eshoo et al.

(10) Patent No.: US 10,550,428 B2
(45) Date of Patent: Feb. 4, 2020

(54) SEQUENCING BY SYNTHESIS USING PULSE READ OPTICS

(71) Applicant: IBIS BIOSCIENCES, INC., Carlsbad, CA (US)

(72) Inventors: Mark W. Eshoo, Carlsbad, CA (US); John M. Clemens, Carlsbad, CA (US); Mark A. Hayden, Carlsbad, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 190 days.

(21) Appl. No.: 15/512,441

(22) PCT Filed: Sep. 16, 2015

(86) PCT No.: PCT/US2015/050376
§ 371 (c)(1),
(2) Date: Mar. 17, 2017

(87) PCT Pub. No.: WO2016/044391
PCT Pub. Date: Mar. 24, 2016

(65) Prior Publication Data
US 2017/0247755 A1  Aug. 31, 2017

Related U.S. Application Data

(60) Provisional application No. 62/051,705, filed on Sep. 17, 2014.

(51) Int. Cl.
*C12Q 1/6869* (2018.01)
*B01L 3/00* (2006.01)
*G01N 21/64* (2006.01)

(52) U.S. Cl.
CPC .......... *C12Q 1/6869* (2013.01); *B01L 3/5085* (2013.01); *G01N 21/648* (2013.01); *G01N 21/6428* (2013.01); *G01N 21/6452* (2013.01); *B01L 2300/0654* (2013.01); *B01L 2300/0829* (2013.01)

(58) Field of Classification Search
None
See application file for complete search history.

(56) References Cited

U.S. PATENT DOCUMENTS

| | | |
|---|---|---|
| 5,695,934 A | 12/1997 | Brenner |
| 5,714,330 A | 2/1998 | Brenner et al. |
| 5,750,341 A | 5/1998 | Macevicz |
| 6,306,597 B1 | 10/2001 | Macevicz |
| 6,432,360 B1 | 8/2002 | Church |
| 6,485,944 B1 | 11/2002 | Church |
| 6,511,803 B1 | 1/2003 | Church et al. |
| 6,787,308 B2 | 9/2004 | Balasubramanian |
| 6,833,246 B2 | 12/2004 | Balasubramanian |
| 6,969,488 B2 | 11/2005 | Bridgham et al. |
| 7,115,400 B1 | 10/2006 | Adessi et al. |
| 7,170,050 B2 | 1/2007 | Turner et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,405,281 B2 | 7/2008 | Xu et al. |
| 7,476,503 B2 | 1/2009 | Turner et al. |
| 7,476,504 B2 | 1/2009 | Turner et al. |
| 8,747,751 B2 | 6/2014 | Reuven et al. |
| 2002/0081582 A1 | 6/2002 | Gao et al. |
| 2005/0009092 A1 | 1/2005 | Brennan |
| 2005/0130173 A1 | 6/2005 | Leamon |
| 2006/0183145 A1* | 8/2006 | Turner .................. B01L 3/5085 435/6.12 |
| 2007/0036511 A1 | 2/2007 | Lundquist et al. |
| 2007/0072196 A1 | 3/2007 | Xu et al. |
| 2007/0077564 A1 | 4/2007 | Roitman et al. |
| 2007/0128133 A1 | 6/2007 | Eid et al. |
| 2007/0134128 A1 | 6/2007 | Korlach |
| 2007/0141598 A1 | 6/2007 | Turner et al. |
| 2007/0161017 A1 | 7/2007 | Eid et al. |
| 2007/0188750 A1 | 8/2007 | Lundquist et al. |
| 2007/0196846 A1 | 8/2007 | Hanzel et al. |
| 2007/0206187 A1 | 9/2007 | Lundquist et al. |
| 2007/0231804 A1 | 10/2007 | Korlach et al. |
| 2007/0238679 A1 | 10/2007 | Rank et al. |
| 2008/0009007 A1 | 1/2008 | Lyle et al. |
| 2008/0030628 A1 | 2/2008 | Lundquist et al. |
| 2008/0032301 A1 | 2/2008 | Rank et al. |
| 2008/0050747 A1 | 2/2008 | Korlach et al. |

(Continued)

FOREIGN PATENT DOCUMENTS

| | | |
|---|---|---|
| CN | 1771336 A | 5/2006 |
| CN | 101914620 A | 12/2010 |

(Continued)

OTHER PUBLICATIONS

Adessi et al."Solid phase DNA amplification: characterisation of primer attachment and amplification mechanisms" Nucleic Acids Res. 2000, 28(20)E87.

(Continued)

*Primary Examiner* — Kaijiang Zhang
(74) *Attorney, Agent, or Firm* — Casimir Jones S.C.; Kirk Hogan

(57) ABSTRACT

Provided herein are systems and methods for nucleic acid sequencing by synthesis in a plurality of wells using detectably labeled chain terminating nucleotides with photolabile blocking groups and pulses of photocleaving light. In certain embodiments, the systems and methods provides a plurality of deblock-scan cycles comprising an initial deblock time period followed by a scanning light period, wherein at least one of the following occurs in each deblock-scan cycle: 1) the deblock time period is shorter than the scan time period; 2) the deblock time period is only long enough to deblock the photolabile groups that are part of a primer in less than all of the plurality of wells; or 3) the deblock time period is between 25 and 150 mSec and the scan time is at least 200 mSec. Such shorter deblock time periods help prevent the addition of more than one nucleotide to the primer prior to scanning (e.g., accuracy is enhanced).

16 Claims, 16 Drawing Sheets

(56) References Cited

U.S. PATENT DOCUMENTS

| | | |
|---|---|---|
| 2008/0080059 A1 | 4/2008 | Dixon et al. |
| 2008/0095488 A1 | 4/2008 | Foquet et al. |
| 2008/0108082 A1 | 5/2008 | Rank et al. |
| 2008/0128627 A1 | 6/2008 | Lundquist et al. |
| 2008/0145278 A1 | 6/2008 | Korlach |
| 2008/0152280 A1 | 6/2008 | Lundquist et al. |
| 2008/0152281 A1 | 6/2008 | Lundquist et al. |
| 2008/0153095 A1 | 6/2008 | Williams et al. |
| 2008/0153100 A1 | 6/2008 | Rank et al. |
| 2008/0157005 A1 | 7/2008 | Lundquist et al. |
| 2008/0160531 A1 | 7/2008 | Korlach |
| 2008/0165346 A1 | 7/2008 | Lundquist et al. |
| 2008/0176241 A1 | 7/2008 | Eid et al. |
| 2008/0176316 A1 | 7/2008 | Eid et al. |
| 2008/0176769 A1 | 7/2008 | Rank et al. |
| 2008/0199874 A1 | 8/2008 | Otto et al. |
| 2008/0199932 A1 | 8/2008 | Hanzel et al. |
| 2008/0206764 A1 | 8/2008 | Williams et al. |
| 2008/0212960 A1 | 9/2008 | Lundquist et al. |
| 2011/0306143 A1 | 12/2011 | Chiou et al. |
| 2012/0156100 A1 | 6/2012 | Tsai et al. |
| 2017/0247755 A1 | 8/2017 | Eshoo et al. |

FOREIGN PATENT DOCUMENTS

| | | | |
|---|---|---|---|
| CN | 102124128 A | 7/2011 | |
| EP | 2305835 | 4/2011 | |
| WO | 2000018957 | 6/2000 | |
| WO | 2006083751 | 8/2006 | |
| WO | 2009155181 | 12/2009 | |
| WO | WO-2009155181 A1 * | 12/2009 | ........ B01L 3/502715 |
| WO | 2011116120 | 9/2011 | |
| WO | 2013105025 | 7/2013 | |
| WO | 2016044391 | 3/2016 | |

OTHER PUBLICATIONS

Bennett et al., "Toward the 1,000 dollars human genome", 2005, Pharmacogenomics, 6, 373-382.

Birren et al., Genome Analysis: Analyzing DNA, 1, Cold Spring Harbor, N.Y.; 1997, TOC Only.

Brenner et al. "Gene expression analysis by massively parallel signature sequencing (MPSS) on microbead arrays" (2000). Nat. Biotechnol. 18:630-634.

International Search Report of related PCT/US2015/050376, dated Dec. 17, 2015,14 pages.

Korlach et al. "Selective aluminum passivation for targeted immobilization of single DNA polymerase molecules in zero-mode waveguide nanostructures" Proc. Nat'l. Acad. Sci. U.S.A., 2008,105(4): 11761181.

Maclean et al., "Application of 'next-generation' sequencing technologies to microbial genetics", Nature Rev. Microbiol.,2009, 7: 287-296.

Margulies et al., "Genome sequencing in microfabricated high-density picolitre reactors" 2005 Nature 437, 376-380.

Mitra et al., 2003,"Fluorescent in situ sequencing on polymerase colonies" Analytical Biochemistry 320, 55-65.

Shendure et al.,"Accurate multiplex polony sequencing of an evolved bacterial genome" Science, 2005, 309, 1728-1732.

Voelkerding et al., "Next-generation sequencing: from basic research to diagnostics", Clinical Chem., 55: 641-658, 2009.

Zhu et al., "Zero-mode waveguides for single-molecule analysis." Annu Rev Biophys. 2012;41:269-93.

Extended European Search Report of related EP 15841893.9, dated Mar. 27, 2018, 10 pages.

Office Action issued in corresponding Chinese Patent Application No. 201580062445.5, dated Dec. 7, 2018, 11 pages.

\* cited by examiner

Ideal
Expected = 0.08789 (fraction of molecules that undergo a color change during each cycle, if there are no homopolymers)
Avg. = 0.08789
SD = 0

20 molecules/400 cycles
Expected = 0.08789
Avg. = 0.087375
SD = 0.064185

40 molecules/400 cycles
Expected = 0.08789
Avg. = 0.090813
SD = 0.047079

80 molecules/400 cycles
Expected = 0.08789
Avg. = 0.090781
SD = 0.032064

- As expected, the standard deviation gets smaller as the number of molecules sampled gets larger.

SEQUENCING BY SYNTHESIS USING PULSE READ OPTICS

FIELD OF THE INVENTION

Provided herein are systems and methods for nucleic acid sequencing by synthesis in a plurality of wells using detectably labeled chain terminating nucleotides with photolabile blocking groups and pulses of photocleaving light. In certain embodiments, the systems and methods provide a plurality of deblock-scan cycles comprising an initial deblock time period followed by a scanning light period, wherein at least one of the following occurs in each deblock-scan cycle: 1) the deblock time period is shorter than the scan time period; 2) the deblock time period is only long enough to deblock the photolabile groups that are part of a primer in less than all of the plurality of wells; or 3) the deblock time period is between 25 and 150 mSec and the scan time is at least 200 mSec. Such shorter deblock time periods help prevent the addition of more than one nucleotide to the primer prior to scanning (e.g., accuracy is enhanced).

BACKGROUND

In sequencing by synthesis with detectably labeled nucleotides with photolabile blocking groups, the time period needed for complete deblocking is relatively long, while the time period of nucleotide incorporation is relatively fast. As a result of the relatively long-deblocking time, additional nucleotides may be incorporated onto the end of the primer sequence before they can be scanned and detected. Therefore, the accuracy of the sequencing reaction may be compromised.

SUMMARY OF THE INVENTION

Provided herein are systems and methods for nucleic acid sequencing by synthesis in a plurality of wells using detectably labeled chain terminating nucleotides with photolabile blocking groups and pulses of photocleaving light. In certain embodiments, the systems and methods provide a plurality of deblock-scan cycles comprising an initial deblock time period followed by a scanning light period, wherein at least one of the following occurs in each deblock-scan cycle: 1) the deblock time period is shorter than the scan time period; 2) the deblock time period is only long enough to deblock the photolabile groups that are part of a primer in less than all of the plurality of wells; or 3) the deblock time period is between 25 and 150 mSec and the scan time is at least 200 mSec. Such shorter deblock time periods, in some embodiments, help prevent the addition of more than one nucleotide to the primer prior to scanning (e.g., accuracy is enhanced).

In some embodiments, provided herein are systems for photocleaving and scanning nucleotide analogs comprising: a) a substrate comprising a plurality of wells which each contain, or are configured to contain, a reaction mixture comprising a template nucleic acid, a polymerase, a primer hybridized to the template, and a first nucleotide analog, wherein the primer comprises a 3' terminal nucleotide analog with a photolabile blocking group that terminates chain extension, and wherein the first nucleotide analog comprises: i) a first detectable moiety, and ii) a photolabile blocking group that terminates chain extension; and b) a light system component comprising: i) a light source in optical communication with the plurality of wells which is configured to provide: A) photocleaving light input that cleaves the photolabile blocking group when it is part of the primer; and B) scanning input light that provides an optical signal from the first detectable moiety after the first nucleotide analog is added to the primer by the polymerase; and ii) a light control component that activates the light source such that a plurality of deblock-scan cycles are generated, wherein each of the deblock-scan cycles comprise an initial deblock time period where at least a part of the photocleaving light input is passed into the plurality of wells, and a following scan time period where at least part of the scanning light input is passed into the plurality of wells, and wherein at least one of the following occurs in each of the deblock-scan cycles: A) the deblock time period is shorter than the scan time period; B) the deblock time period is only long enough to deblock the photolabile blocking groups that are part of the primer in less than all of the plurality of wells; and C) the deblock time period is between 25 and 150 mSec and the scan time is at least 200 mSec.

In certain embodiments, provided herein are systems comprising a light component, wherein the light component is configured to optically interface with a substrate component, wherein the substrate component comprises a plurality of wells, wherein each well contains, or is configured to contain, a reaction mixture comprising a template nucleic acid, a polymerase, a primer hybridized to the template, and a first nucleotide analog, wherein the primer comprises a 3' terminal nucleotide analog with a photolabile blocking group that terminates extension, and wherein the first nucleotide analog comprises: i) a detectable moiety, and ii) a photolabile blocking group that terminates chain extension; and wherein the light component comprises: a) a light source in optical communication with the plurality of wells that provides: A) photocleaving light input that cleaves the photolabile blocking group when it is part of the primer; and B) scanning input light that produces an optical signal from the first detectable moiety after the first nucleotide analog is added to the primer by the polymerase; and b) a light control component that activates the light source such that a plurality of deblock-scan cycles are generated, wherein each of the deblock-scan cycles comprise an initial deblock time period where at least part of the photocleaving light input is passed into the plurality of wells, and a following scan time period where at least part of the scanning light input is passed into the plurality of wells, and wherein at least one of the following occurs in each of the deblock-scan cycles: i) the deblock time period is shorter than the scan time period; ii) the deblock time period is only long enough to deblock the photolabile blocking groups that are part of the primer in less than all of the plurality of wells; and iii) the deblock time period is between 25 and 150 mSec and the scan time is at least 200 mSec.

In particular embodiments, provided herein are methods for photocleaving and detecting nucleotide analogs using a system comprising: i) a substrate comprising a plurality of wells, wherein each well contains a reaction mixture comprising a template nucleic acid, a polymerase, a primer hybridized to the template, and a first nucleotide analog, wherein the primer comprises a 3' terminal nucleotide analog with a photolabile blocking group that terminates chain extension, and wherein the first nucleotide analog comprises: i) a first detectable moiety, and ii) a photolabile blocking group that terminates chain extension; and ii) a light system component comprising: A) a light source in optical communication with the plurality of wells, wherein the light source provides: I) photocleaving light input; and II) scanning light input; B) a light control component that activates the light source such that a plurality of deblock-scan cycles are generated which comprise: I) an initial deblock time period where at least a portion of the photocleaving light input is passed into the wells, and II) a following scan time period where at least a portion of the scanning light input is passed into the wells, iii) a detector component in optical communication with the plurality of optical sensing wells, wherein the method comprises; and b) activating the light control component such that the light source component provides a plurality of the deblock-scan cycles which delock the photolabile blocking groups, when the photolabile blocking groups are part of the primer, in at least some of the wells and generates an optical signal from the detectable moiety in the plurality of wells after the first nucleotide analog is added to the primer by the polymerase, wherein at least one of the following occurs in each of the deblock-scan cycles: A) the deblock time period is shorter than the scan time period; B) the deblock time period is only long enough to deblock the photolabile blocking groups that are part of the primer in less than all of the plurality of wells; and C) the deblock time period is between 25 and 150 mSec and the scan time is at least 200 mSec; and c) detecting the optical signal from detectable moiety generated during each of the plurality of deblock-scan cycles in the plurality of wells with the detector component.

In some embodiments, provided herein are systems comprising a light component, wherein the light component is configured to optically interface with a substrate component, wherein the substrate component comprises a plurality of wells (e.g., optical sensing wells), wherein each of the wells is sized to provide an internal waveguide (e.g., a zero mode waveguide) and/or is optically coupled to an external waveguide (e.g., a planar waveguide), wherein each well contains, or is configured to contain, a reaction mixture comprising a template nucleic acid, a polymerase, a primer hybridized to the template, and a first nucleotide analog, wherein the primer comprises a 3' terminal nucleotide analog with a photolabile blocking group that terminates extension, and wherein the first nucleotide analog comprises: i) a detectable moiety, and ii) a photolabile blocking group that terminates chain extension; and wherein the light component comprises: a) a light source in optical communication with the internal and/or external waveguides, wherein the light source is configured to provide: A) photocleaving light input that, when passed into the internal or external waveguides, generates a first electromagnetic wave (e.g., evanescent wave) in the optical sensing wells that is capable of cleaving the photolabile blocking groups when they are part of the primer; and B) scanning input light that, when passed into the internal or external waveguides, generates a second electromagnetic wave (e.g., evanescent wave) in the optical sensing wells that is capable of producing an optical signal from the detectable moiety after the first nucleotide analog is added to the primer; and b) a light control component configured to activate the light source such that a plurality of deblock-scan cycles are generated, wherein each of the deblock-scan cycles comprise an initial deblock time period where the photocleaving light input is passed into the internal and/or external waveguides, and a following scan time period where the scanning light input is passed into the internal and/or external waveguides, and wherein at least one of the following occurs in each of the deblock-scan cycles: A) the deblock time period is shorter than the scan time period; B) the deblock time period is only long enough to deblock the photolabile blocking groups that are part of the primer in less than all of the plurality of optical sensing wells; and C) the deblock time period is between 25 and 150 mSec and the scan time is at least 200 mSec.

In certain embodiments, provided herein are systems for system for photocleaving and scanning nucleotide analogs comprising: a) a substrate comprising a plurality of optical sensing wells, wherein each of the optical sensing wells is sized to provide an internal waveguide and/or is optically coupled to an external waveguide, wherein each optical sensing well contains, or is configured to contain, a reaction mixture comprising a template nucleic acid, a polymerase, a primer hybridized to the template, and a first nucleotide analog, wherein the primer comprises a 3' terminal nucleotide analog with a photolabile blocking group that terminates chain extension, and wherein the first nucleotide analog comprises: i) a first detectable moiety, and ii) a photolabile blocking group that terminates chain extension; and b) a light system component comprising: i) a light source in optical communication with the internal and/or external waveguides, wherein the light source is configured to provide: A) photocleaving light input that, when passed into the internal or external waveguides, generates a first electromagnetic wave (e.g., evanescent wave) in the optical sensing wells that is capable of cleaving the photolabile blocking group when it is part of the primer; and B) scanning input light that, when passed into the internal or external waveguides, generates a second electromagnetic wave (e.g., evanescent wave) in the optical sensing wells that is capable of producing an optical signal from the first detectable moiety after the first nucleotide analog is added to the primer by the polymerase; and ii) a light control component configured to activate the light source such that a plurality of deblock-scan cycles are generated, wherein each of the deblock-scan cycles comprise an initial deblock time period where the photocleaving light input is passed into the internal and/or external waveguides, and a following scan time period where the scanning light input is passed into the internal and/or external waveguides, and wherein at least one of the following occurs in each of the deblock-scan cycles: A) the deblock time period is shorter than the scan time period; B) the deblock time period is only long enough to deblock the photolabile blocking groups that are part of the primer in less than all of the plurality of optical sensing wells; and C) the deblock time period is between 25 and 150 mSec and the scan time is at least 200 mSec.

In particular embodiments, provided herein are methods for photocleaving and detecting nucleotide analogs using a system comprising: i) a substrate comprising a plurality of optical sensing wells, wherein each of the optical sensing wells is sized to provide an internal waveguide and/or is optically coupled to an external waveguide, wherein each optical sensing well contains a reaction mixture comprising a template nucleic acid, a polymerase, a primer hybridized to the template, and a first nucleotide analog, wherein the primer comprises a 3' terminal nucleotide analog with a photolabile blocking group that terminates chain extension, and wherein the first nucleotide analog comprises: i) a first detectable moiety, and ii) a photolabile blocking group that terminates chain extension; and ii) a light system component comprising: A) a light source in optical communication with the internal and/or external waveguides, wherein the light source provides: I) photocleaving light input that generates a first electromagnetic wave in the optical sensing wells when passed into the internal or external waveguides; and II) scanning input light that generates a second electromagnetic wave in the optical sensing wells when passed into the internal or external waveguides; B) a light control component configured to activate the light source such that a plurality of deblock-scan cycles are generated which comprise: I) an initial deblock time period where the photocleaving light input is passed into the internal and/or external waveguides, and II) a following scan time period where the scanning light input is passed into the internal and/or external waveguides, iii) a detector component in optical communication with the plurality of optical sensing wells, wherein the method comprises: activating the light control component such that the light source component provides a plurality of the deblock-scan cycles which delock the photolabile blocking groups, when they are part of the primer, in at least some of the optical sensing wells and generates an optical signal from the detectable moiety in the plurality of optical sensing wells after the first nucleotide analog is added to the primer by the polymerase, wherein at least one of the following occurs in each of the deblock-scan cycles: A) the deblock time period is shorter than the scan time period; B) the deblock time period is only long enough to deblock the photolabile blocking groups that are part of the primer in less than all of the plurality of optical sensing wells; and C) the deblock time period is between 25 and 150 mSec and the scan time is at least 200 mSec; and c) detecting the optical signal from detectable moiety generated during each of the plurality of deblock-scan cycles in the plurality of optical sensing wells with the detector component.

In particular embodiments, the detecting provides sequence information for at least a portion of the template nucleic acid in at least some of the plurality of wells (e.g., the identity of 5 bases . . . 10 bases . . . or more; or the complete sequence of the template). In certain embodiments, the light control component comprises a user interface, and wherein the activating is performed by a user through the user interface. In further embodiments, the user interface comprises a computer keyboard and/or computer mouse. In particular embodiments, the methods are performed without any washing step (e.g., single reaction mixture in well during entire sequence by synthesis reaction).

In some embodiments, the systems further comprise c) a detector component in optical communication with the plurality of wells which is capable of detecting the optical signal from the plurality of wells. In certain embodiments, the system further comprises a filter, where said optical signal passes through said filter prior to being detected by said detector. In certain embodiments, the light control component comprises a computer processor and a computer program embedded within the computer processor, wherein the computer program that controls the light source such that the plurality of deblock-scan cycles are generated.

In particular embodiments, the substrate is composed of a material selected from the group consisting of: transparent glass, transparent plastic, silicon-titanium oxide, titanium oxide, tantalum oxide, niobium oxide, hafnium oxide, aluminum oxide, zirconium oxide, silicon nitride, aluminum nitride, titanium nitride, polycarbonate (PC), PMMA, or Su8. In other embodiments, the plurality of wells comprises at least 5 wells (e.g., at least 5 . . . 25 . . . 100 . . . 250 . . . 500 . . . 1000 . . . 2000 . . . 4000 . . . 8000 . . . 50,000 . . . or more).

In particular embodiments, the plurality of wells are sized to provide an internal waveguide (e.g., an internal waveguide at the bottom of said wells). In certain embodiments, each of the plurality of wells comprises a zero-mode waveguide. In particular embodiments, the systems further comprise one or a plurality of external waveguides (e.g., an external waveguide for each of the plurality of optically sensing wells). In particular embodiments, the plurality of wells have a volume between 200 nanoliters and 10 zeptoliters. In further embodiments, the plurality of wells are optically coupled to an external waveguide. In additional embodiments, each of the wells contains the reaction mixture.

In certain embodiments, the template nucleic acid in each of the plurality of wells is part of a sequencing library (e.g., human genomic sequencing library). In further embodiments, the photolabile blocking group that is part of the primer is the same as, or different from, the photolabile blocking group that is part of the first nucleotide analog. In other embodiments, the reaction mixture further comprises a second nucleotide analog (e.g., a second type of nucleotides analog) comprising a photolabile locking group and a second detectable moiety different from the first detectable moiety, wherein the first and second nucleotide analogs have different bases (e.g., selected from guanine, cytosine, adenine, and thymine). In other embodiments, the polymerase comprises a Phi29 polymerase or mutant thereof.

In additional embodiments, the first detectable moiety comprises a fluorescent dye. In further embodiments, the photolabile blocking group is selected from the group consisting of: an o-nitrobenzyl blocking group, nitroveratryl, 1-pyrenylmethyl, 6-nitroveratryloxycarbonyl, dimethyl-dimethoxybenzyloxycarbonyl, 2-nitrobenzyloxycarbonyl, 5-bromo-7-nitroindolinyl, O-hydroxy-alpha-methyl-cinnamoyl, methyl, 6-nitroveratryloxycarbonyl, methyl-6-nitropiperonyloxycarbonyl, and 2-oxymethylene anthraquinone, dimethoxybenzyloxy carbonyl, 5-bromo-7-nitroindolinyl, o-hydroxy-alpha-methyl cinnamoyl, and 2-oxymethylene anthriquinone.

In additional embodiments, the light source comprises a first light generating component configured to generate the photocleaving light input, and a second light generating component configured to generate the scanning light input. In other embodiments, the light source comprises a light generating component configured to alternately generate both the photocleaving light input and the scanning light input. In additional embodiments, the photocleaving light input has a wavelength between 300 nm and 2000 nm (e.g., 300 nm . . . 500 nm . . . 800 nm . . . 1200 nm . . . 1500 nm . . . and 2000 nm). In other embodiments, the scanning light input has a wavelength between 230 nm and 1000 nm (e.g., 230 nm . . . 450 . . . 680 . . . 850 . . . and 1000 nm). In further embodiments, the photocleaving light input has a wavelength different than that of the scanning light input wavelength.

In certain embodiments, the external waveguide comprises one or more planar waveguides. In further embodiments, the plurality of wells are optically coupled to an external waveguide, wherein the external waveguide is either one waveguide in optical communication with all of the plurality of wells, or wherein the external waveguide is a plurality of waveguides, one for each of the plurality of wells.

In additional embodiments, the first and/or second electromagnetic waves comprises an evanescent wave or a traveling field wave. In further embodiments, the light control component comprises a user interface that allows a user to activate the light source. In additional embodiments, the plurality of deblock-scan cycles is at least five deblock-scan cycles (e.g., at least 5 . . . 10 . . . 15 . . . 25 . . . 100 . . . 1000 or more). In further embodiments, the deblock time period is shorter than the scan time period. In additional embodiments, the deblock time period is 5% shorter than the scan time period (e.g., 5% . . . 15% . . . 25% . . . 50% . . . 68% . . . 75% . . . 90% . . . 95% . . . or 99% shorter).

In particular embodiments, the deblock time period is only long enough to deblock the photolabile blocking groups that are part of the primer in less than all of the plurality of wells. In further embodiments, the deblock time period is only long enough to deblock the photolabile blocking groups that are part of the primer in about 7-12 percent, or about 12-25%, or about 25-55% of the plurality of wells. In certain embodiments, the deblock time period is between 15 and 150 mSec (e.g., 15 . . . 25 . . . 50 . . . 75 . . . 100 . . . 125 . . . and 150 mSec) and the scan time is at least 200 mSec (e.g., at least 200 mSec . . . 500 mSec . . . 750 mSec . . . 1 second . . . 1.5 seconds . . . 2 seconds . . . 5 seconds . . . 10 seconds . . . or more).

DESCRIPTION OF THE FIGURES

FIG. 8a models cycle 0, where there are $10^6$ molecules on the surface waiting to be deblocked. At cycle 1 (shown in FIG. 8b), 8.8% of the $10^6$ molecules on the surface will be deprotected and extended (darker/blue bar), while 91.2% will remain blocked (lighter bar). FIG. 8c shows 5 cycles, FIG. 8d shows 10 cycles, FIG. 8e shows 15 cycles, and FIG. 8f shows 20 cycles. FIG. 8f shows that a normal distribution is starting to appear. As shown in FIG. 8g (25 cycles), the distribution curve is slowly moving to the right, while the distribution itself is slowly diminishing and becoming more spread out, with each successive cycle. FIG. 8h shows the distribution after 30 cycles. As shown in FIG. 8i (35 cycles), the normal distribution continues to diminish and spread out, much like Poisson distribution at high copy number. The 35 cycles in FIG. 8i represents about 3 minutes of sequencing run time.

FIG. 12 shows a mathematical model for detecting homopolymers by short pulses of deprotecting light.

DETAILED DESCRIPTION

Figure 1:
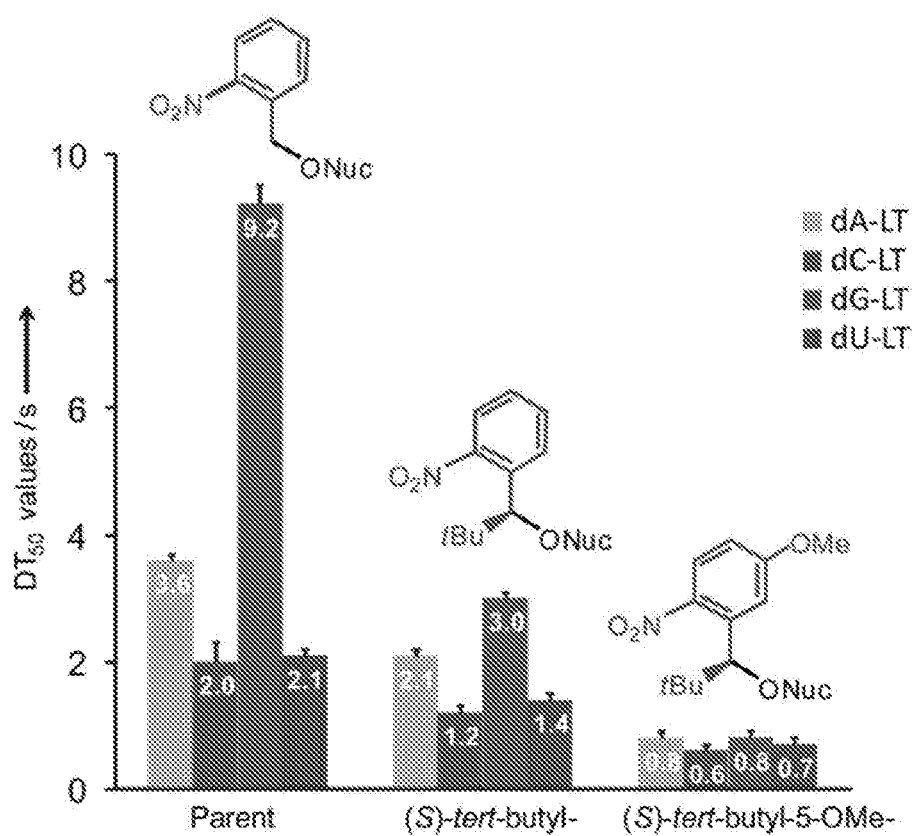
FIG. 1 shows the DT50 (time required to deblock 50% of the molecules) for a number of Lasergen dNTP analogues.

Provided herein are systems and methods for nucleic acid sequencing by synthesis in a plurality of wells using detectably labeled chain terminating nucleotides with photolabile blocking groups and pulses of photocleaving light. In certain embodiments, the systems and methods provides a plurality of deblock-scan cycles comprising an initial deblock time period followed by a scanning light period, wherein at least one of the following occurs in each deblock-scan cycle: 1) the deblock time period is shorter than the scan time period; 2) the deblock time period is only long enough to deblock the photolabile groups that are part of a primer in less than all of the plurality of wells; or 3) the deblock time period is between 25 and 150 mSec and the scan time is at least 200 mSec. Such shorter deblock time periods help prevent the addition of more than one nucleotide to the primer prior to scanning (e.g., accuracy is enhanced).

The present description is not limited to the type of sequencing approach that is used with the photolabile blocked nucleotides and deblock-scan cycles provided herein. In certain embodiments, sequence by synthesis methods are employed. Exemplary sequencing methods are detailed further below. In certain embodiments, the deblock-scan cycles described herein are used with sequencing methodologies that employ Zero-mode waveguides (e.g., as produced by Pacific Biosciences). In an exemplary embodiments, a sequencing by synthesis approach using a zero mode wave guide ZMWG and a photo-deblockable nucleotide is used to enable a single fluid sequencing by synthesis process. The ZMWG is used, for example, to both detect the detectably (e.g., flourescently) labeled nucleotide in the acceptor site of a polymerase and to selectively deblock this nucleotide while not deblocking the nucleotides in the reaction buffer that are outside the illumination field of the ZMWGs. Such an approach allows single molecule sequencing by synthesis. The challenge is the time domains for de-blocking (relatively slow) and nucleotide incorporation (relatively fast) may not be compatible for accurate sequencing as additional nucleotides may be incorporated during the relatively longer de-blocking step.

The present description overcomes such issues with timing and accuracy. For example, the deblock-scan cycles described herein breakup the de-blocking time into pulses followed by reads. For example if it take 5 seconds to efficiently de-block 99% of the nucleotides in the polymerase and 200 mSec to incorporate a nucleotide, then one pulse (with photocleaving light) for a brief period of time, for example 50 mSec, and then read the base (using scanning light and a detector). In this way, changes in the nucleotide sequence are detected and the de-blocking time is, for example, significantly shorter than the incorporation time. In addition, in certain embodiments, one detects the molecules that are still waiting to accept the next nucleotide as being without a labeled nucleotide to enable accurate sequencing of homopolymeric sequences. In this regard, the systems and methods described herein allows a single fluid (e.g., no washing required) single molecule sequencing by synthesis when the time domains for photo de-blocking and nucleotide incorporation are not compatible.

As indicated above, the present description is not limited to any particular sequencing technology that can employ photolabile blocked nucleotides and the deblock-scan cycles described herein. In certain embodiments, the sequencing by synthesis methods employ waveguides (e.g., planar, zero-mode waveguides, etc.). In certain embodiments, such methods are described in the following publications: U.S. Pat. Nos. 7,476,504; 8,747,751; Pat. Pub. 20110306143; and Pat. Pub. 20120156100; all of which are herein incorporated by reference in their entireties. These four publications are specifically incorporated by reference, including the figures and descriptions of the figures, as if fully set forth herein.

Again, the present description is not limited to any particular sequencing technology that can employ photolabile blocked nucleotides and the deblock-scan cycles described herein. One real-time single molecule sequencing system that is employed is that developed by Pacific Biosciences that employs Zero Mode Wave Guides (ZMWs), and described in Voelkerding et al., *Clinical Chem.*, 55: 641-658, 2009; MacLean et al., *Nature Rev. Microbiol.*, 7: 287-296; U.S. Pat. Nos. 7,170,050; 7,302,146; 7,313,308; 7,476,503; all of which are herein incorporated by reference. In general, such methods utilizes reaction wells 50-100 nm in diameter and encompassing a reaction volume of approximately 20 zeptoliters ($10 \times 10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera. With this technology, DNA sequencing is generally performed on SMRT chips, each containing thousands of zero-mode waveguides (ZMWs). A ZMW is a hole/well, tens of nanometers in diameter, fabricated in a 100 nm metal film deposited on a silicon dioxide substrate. Each ZMW becomes a nanophotonic visualization chamber providing a detection volume of just 20 zeptoliters (10-21 liters). At this volume, the activity of a single molecule is detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides (would be blocked with photolabile blocking groups for the systems and methods described herein), each type labeled with a different colored fluorophore, are then introduced into the reaction solution at high concentrations which promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Other processes and systems that may be adapted to employ photolabile blocked nucleotides the deblock-scan cycles provides herein are described in, for example, U.S. Pat. No. 7,405,281, entitled "Fluorescent nucleotide analogs and uses therefor;" U.S. Pat. No. 7,315,019, entitled "Arrays of optical confinements and uses thereof;' U.S. Pat. No. 7,313,308, entitled "Optical analysis of molecules," U.S. Pat. No. 7,302,146, entitled "Apparatus and method for analysis of molecules", and U.S. Pat. No. 7,170,050, entitled "Apparatus and methods for optical analysis of molecules," U.S. Patent Publications Nos. 20080212960, entitled "Methods and systems for simultaneous real-time monitoring of optical signals from multiple sources", 20080206764, entitled "Flowcell system for single molecule detection", 20080199932, entitled "Active surface coupled polymerases", 20080199874, entitled "CONTROLLABLE STRAND SCISSION OF MINI CIRCLE DNA", 20080176769, entitled "Articles having localized molecules disposed thereon and methods of producing same", 20080176316, entitled "Mitigation of photodamage in analytical reactions", 20080176241, entitled "Mitigation of photodamage in analytical reactions", 20080165346, entitled "Methods and systems for simultaneous real-time monitoring of optical signals from multiple sources", 20080160531, entitled "Uniform surfaces for hybrid material substrates and methods for making and using same", 20080157005, entitled "Methods and systems for simultaneous real-time monitoring of optical signals from multiple sources", 20080153100, entitled "Articles having localized molecules disposed thereon and methods of producing same", 20080153095, entitled "CHARGE SWITCH NUCLEOTIDES", 20080152281, entitled "Substrates, systems and methods for analyzing materials", 20080152280, entitled "Substrates, systems and methods for analyzing materials", 20080145278, entitled "Uniform surfaces for hybrid material substrates and methods for making and using same", 20080128627, entitled "SUBSTRATES, SYSTEMS AND METHODS FOR ANALYZING MATERIALS", 20080108082, entitled "Polymerase enzymes and reagents for enhanced nucleic acid sequencing", 20080095488, entitled "SUBSTRATES FOR PERFORMING ANALYTICAL REACTIONS", 20080080059, entitled "MODULAR OPTICAL COMPONENTS AND SYSTEMS INCORPORATING SAME", 20080050747, entitled "Articles having localized molecules disposed thereon and methods of producing and using same", 20080032301, entitled "Articles having localized molecules disposed thereon and methods of producing same", 20080030628, entitled "Methods and systems for simultaneous real-time monitoring of optical signals from multiple sources", 20080009007, entitled "CONTROLLED INITIATION OF PRIMER EXTENSION", 20070238679, entitled "Articles having localized molecules disposed thereon and methods of producing same", 20070231804, entitled "Methods, systems and compositions for monitoring enzyme activity and applications thereof", 20070206187, entitled "Methods and systems for simultaneous real-time monitoring of optical signals from multiple sources", 20070196846, entitled "Polymerases for nucleotide analogue incorporation", 20070188750, entitled "Methods and systems for simultaneous real-time monitoring of optical signals from multiple sources", 20070161017, entitled "MITIGATION OF PHOTODAMAGE IN ANALYTICAL REACTIONS", 20070141598, entitled "Nucleotide Compositions and Uses Thereof", 20070134128, entitled "Uniform surfaces for hybrid material substrate and methods for making and using same", 20070128133, entitled "Mitigation of photodamage in analytical reactions", 20070077564, entitled "Reactive surfaces, substrates and methods of producing same", 20070072196, entitled "Fluorescent nucleotide analogs and uses therefore", and 20070036511, entitled "Methods and systems for monitoring multiple optical signals from a single source", and Korlach et al. (2008) "Selective aluminum passivation for targeted immobilization of single DNA polymerase molecules in zero-mode waveguide nanostructures" Proc. Nat'l. Acad. Sci. U.S.A. 105(4): 11761181—all of which are herein incorporated by reference in their entireties.

Other sequencing methodologies that may be adapted to employ the photolabile blocked nucleotides and deblock-scan cycles described herein are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, DNA sequencing is achieved by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties) the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties) and the Adessi PCR colony technology (Adessi et al. (2000). Nucleic Acid Res. 28, E87; WO 00018957; herein incorporated by reference in its entirety).

Another sequencing methodology that may be adapted to employ the photolabile blocked nucleotides and deblock-scan cycles described herein is the Solexa/Illumina platform. In the Solexa/Illumina platform (Voelkerding et al., *Clinical Chem.*, 55: 641-658, 2009; MacLean et al., *Nature Rev. Microbiol.*, 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

EXAMPLES

Example 1

Deprotection Time of Blocked Nucleotides

Figure 2:
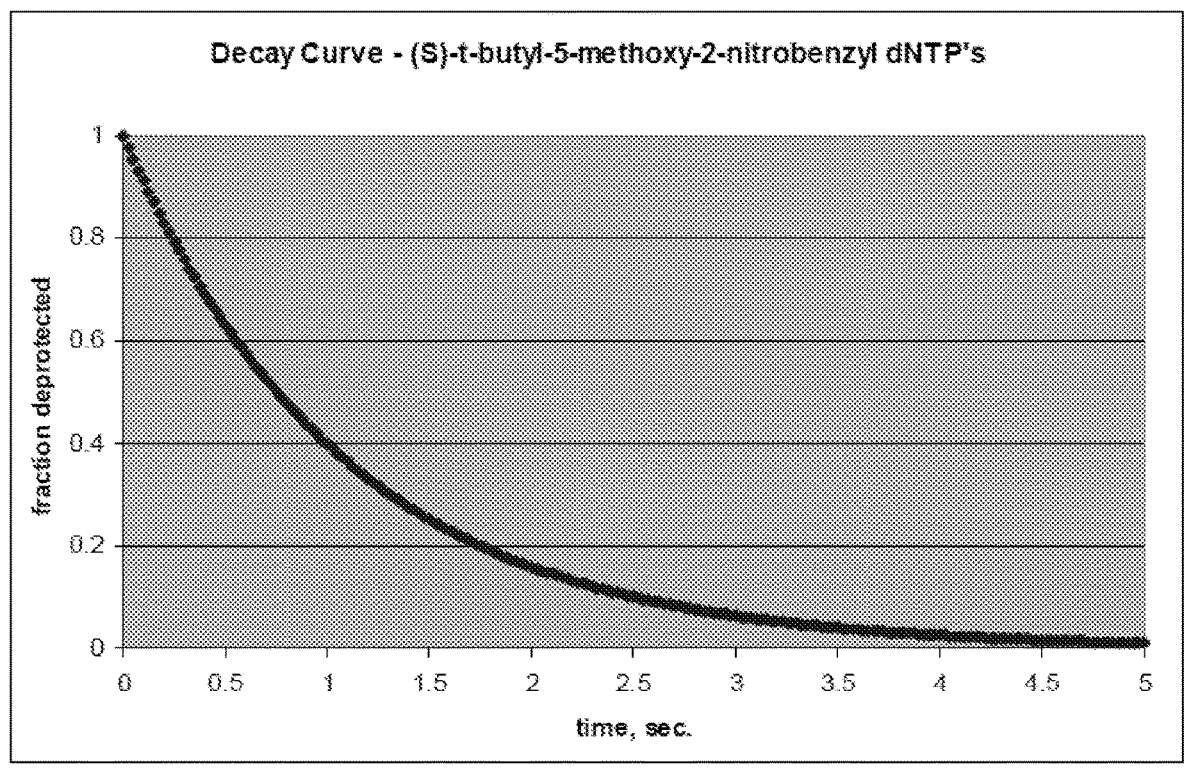
FIG. 2 shows a decay curve for a blocked base ((S)-t-butyl-5-methoxy-2-nitrobenzyl dNTP) with a $t_{1/2}$ of 750 mSec.
Figure 3:
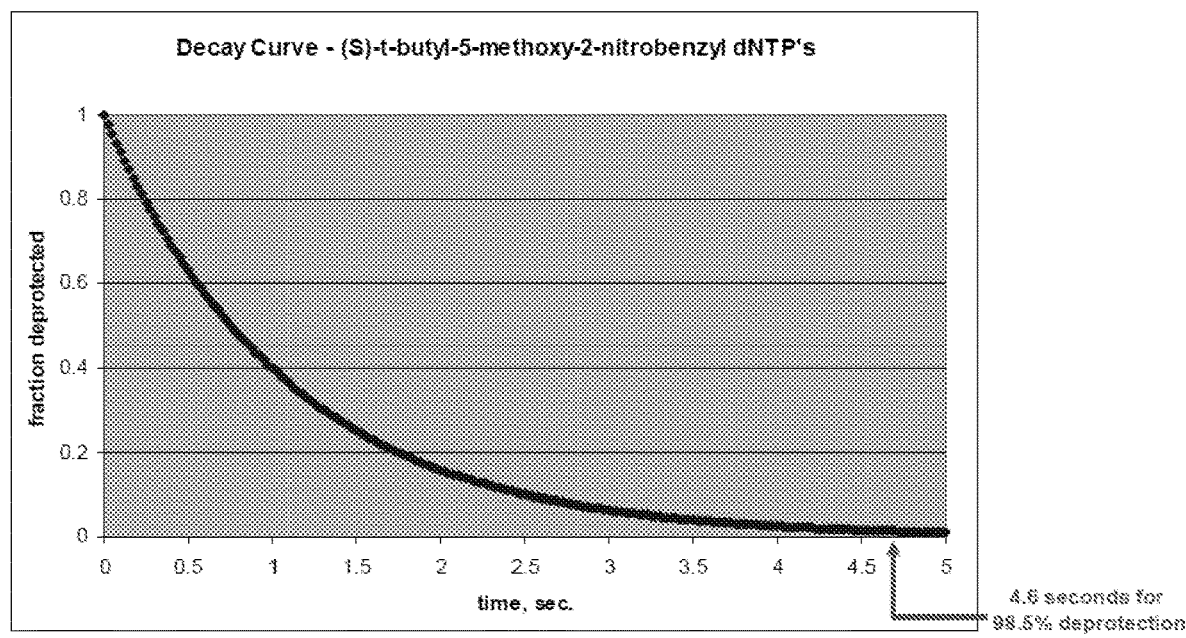
FIG. 3 shows, based on the curve in FIG. 2, a deprotection time of 4.6 seconds is required to deprotect 98.5% of the dNTP's.
Figure 4:
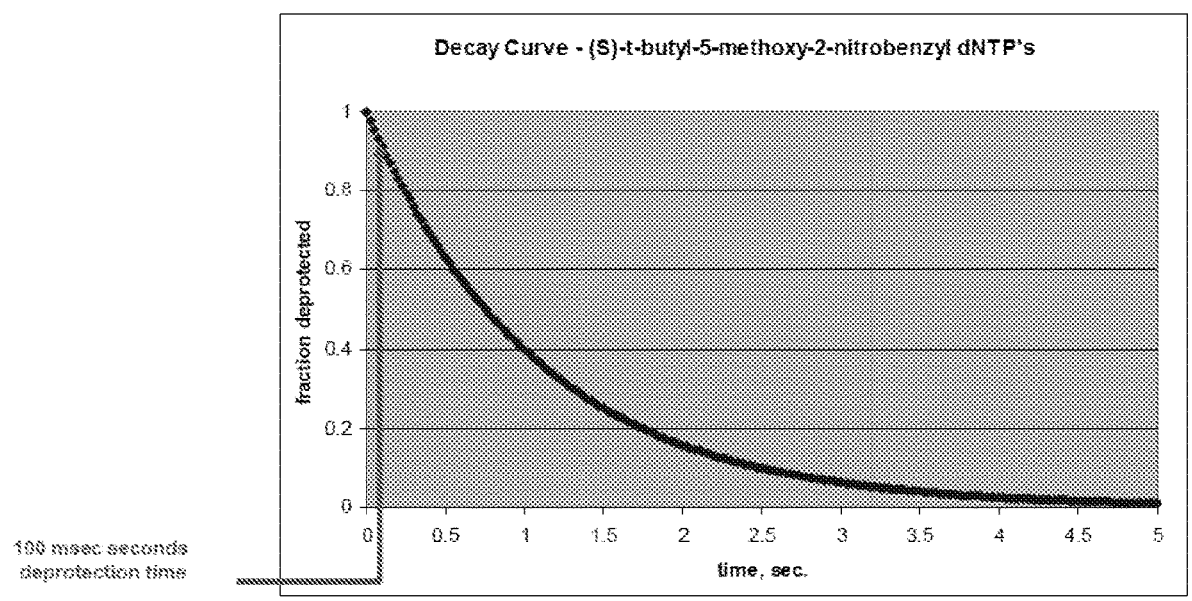
FIG. 4 shows that a rapid light pulse of 100 msec, for example, could then be used to eliminate the problem of spurious base addition.

The most recent generation of Lasergen's dNTP protected analogues have a DT50 of approximately 750 msec (time required to deblock 50% of the molecules). The DT50 for three Lasergen dNTP analogues is shown in FIG. 1. A t1/2 of 750 msec gives the decay curve in solution shown in FIG. 2. Based on this curve, a deprotection time of 4.6 seconds is required to deprotect 98.5% of the dNTP's (as shown in FIG. 3). This is required for every cycle using the standard "wash" approach, where unincorporated nucleotides are removed before deprotection. As shown in FIG. 4, a rapid light pulse of 100 msec, for example, is used to eliminate the problem of spurious base addition. Therefore, a fast light pulse, followed by a longer read time (for single molecules) generally limits base extension to single base only, thereby increasing sequencing accuracy.

Figure 5:
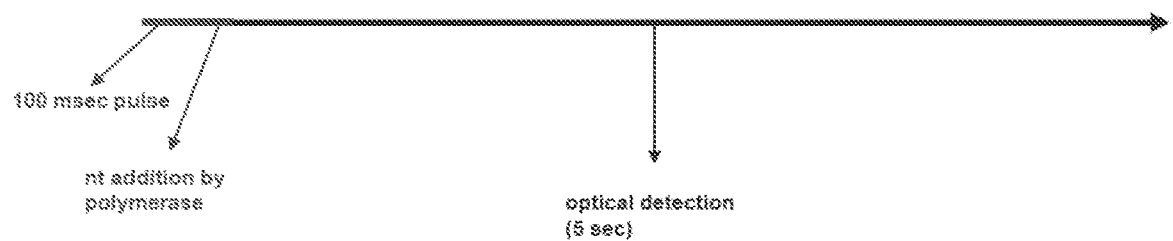
FIG. 5 shows that, given the extension rate of standard DNA polymerase on a surface is approximately 5 bases/sec, it would be expected that the new base incorporated after the 100 msec pulse would be relatively rapid.
Figure 6:
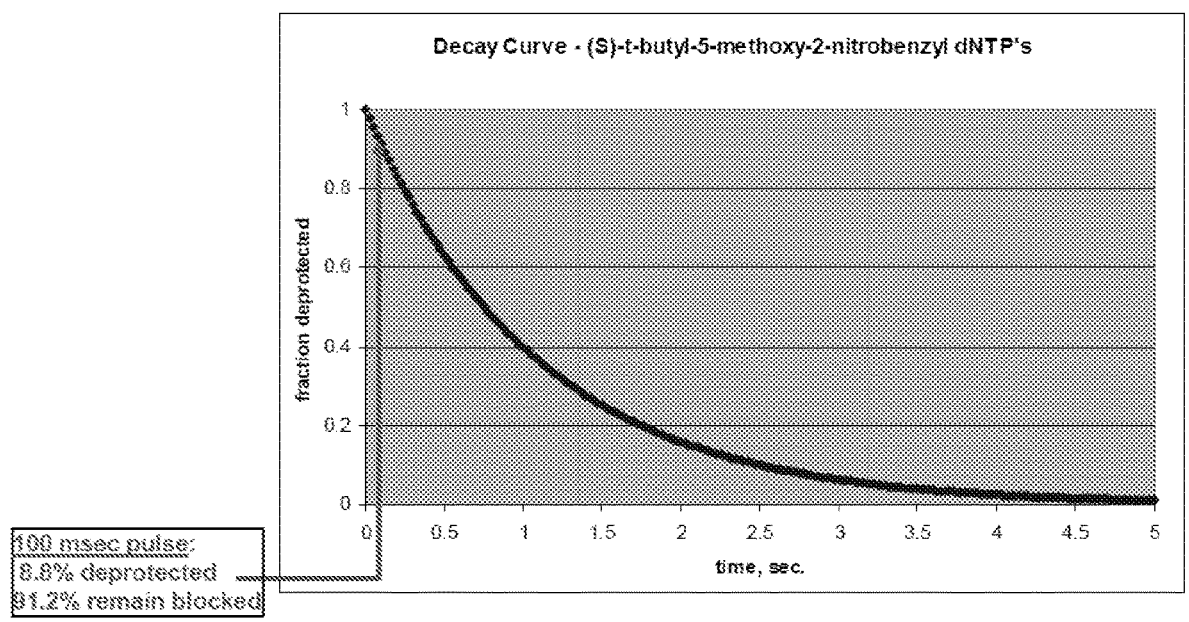
FIG. 6 shows that the kinetics of deprotection can be derived from the standard decay curve, resulting in the deprotection ratio shown in this figure.

Given the extension rate of standard DNA polymerase on a surface is approximately 5 bases/sec, the new base incorporated after the 100 msec pulse is relatively rapid as shown in the time sequence in FIG. 5. FIG. 5 uses an arbitrary detection time of 5 seconds for demonstration purposes only. Under this scenario, the kinetics of deprotection is derived from the standard decay curve. This results in the deprotection ratio shown in FIG. 6.

The base addition mechanism, for this example, can be modeled using the Binomial Expansion equation:

$$(X+Y)^N$$

Figure 7:
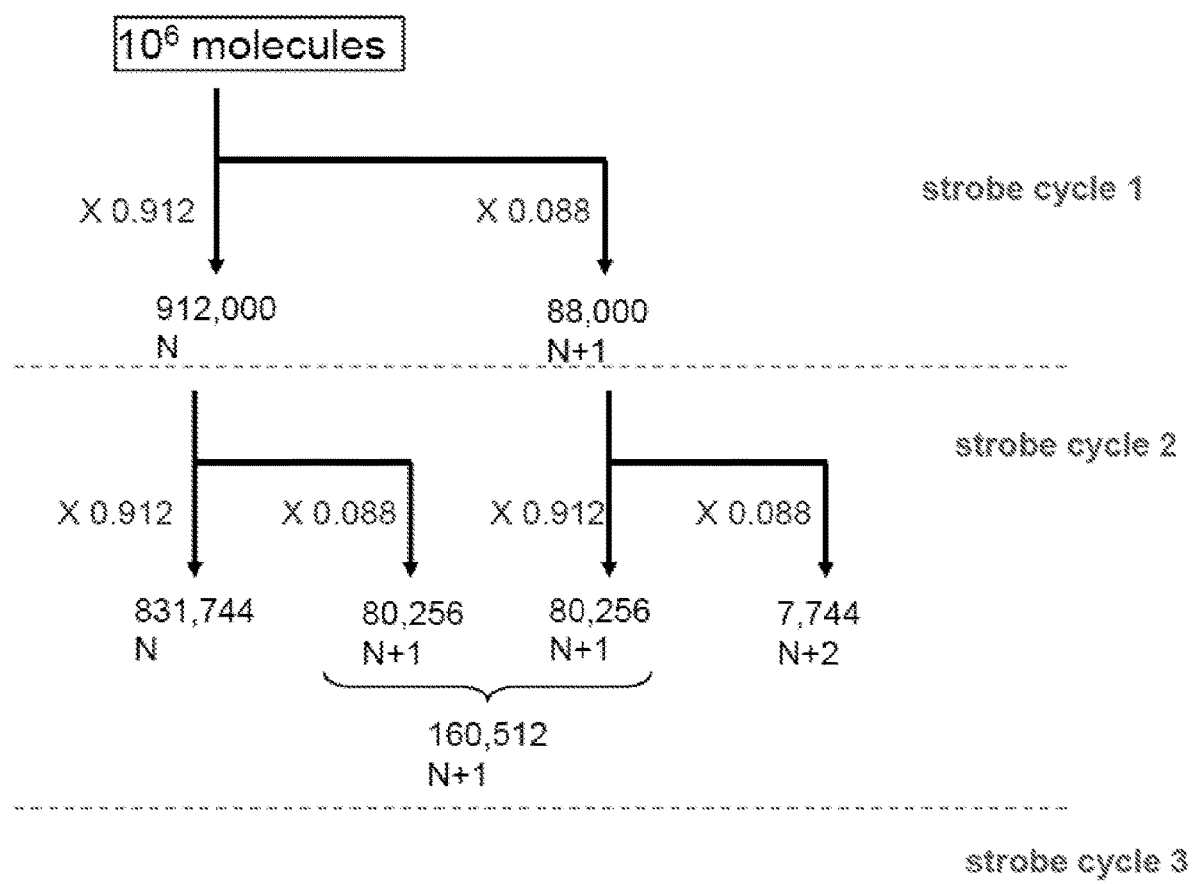
FIG. 7 shows three strobe cycles, using $10^6$ molecules in the binomial expansion model described in Example 1 below.

In this case, X=fraction of molecules remaining blocked after 100 msec light pulse; Y=fraction of molecules deprotected after 100 msec light pulse; and N=cycle number. For the present example, X=0.9121; and Y=0.0879. This ratio remains constant for each strobe cycle since a total of $10^6$ molecules either have an existing base or a new base after each detection phase. Three strobe cycles, using $10^6$ molecules in the binomial expansion model, are shown in FIG. 7.

In the present hypothetical example, the strobe flashes are intermixed with a 5-sec detection step. Producing multiple strobe flashes serially (before a detection read) was not done since this would not give any advantage over a long deprotect time. It is generally assumed for this example, that enough light makes it to the surface to mimic deprotection kinetics in solution. In this example, each light pulse will deprotect 8.8% of the molecules on the surface (from decay curve). Nucleotide addition occurs rapidly after deprotection.

Figure 8:
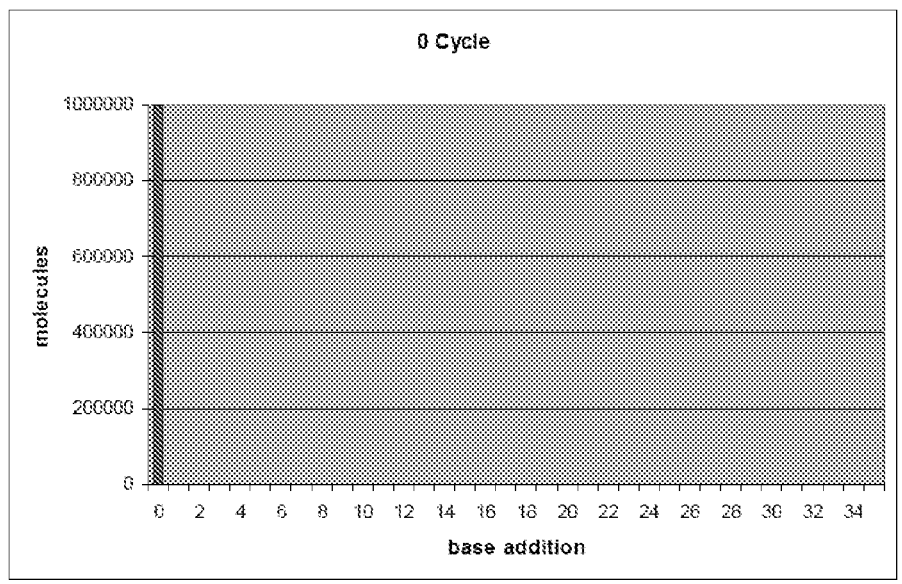
FIGS. 8a-i model 35 strobe cycles starting off with $10^6$ target molecules on a surface as described in Example 1.
Figure 8:
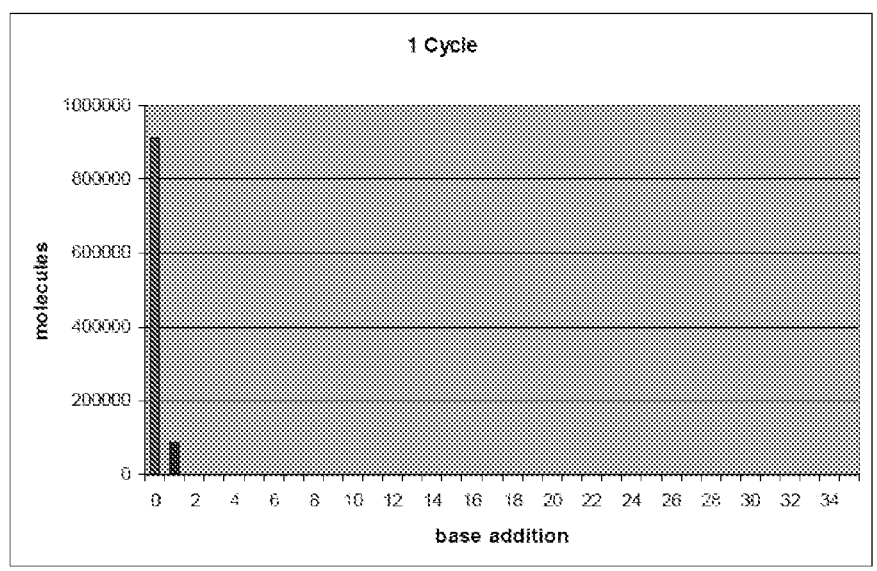
Figure 8:
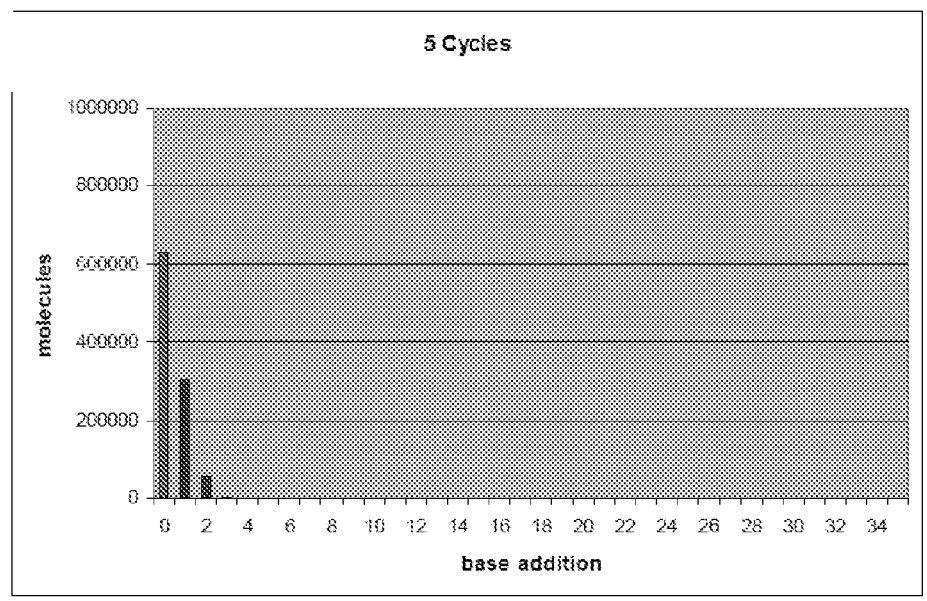
Figure 8:
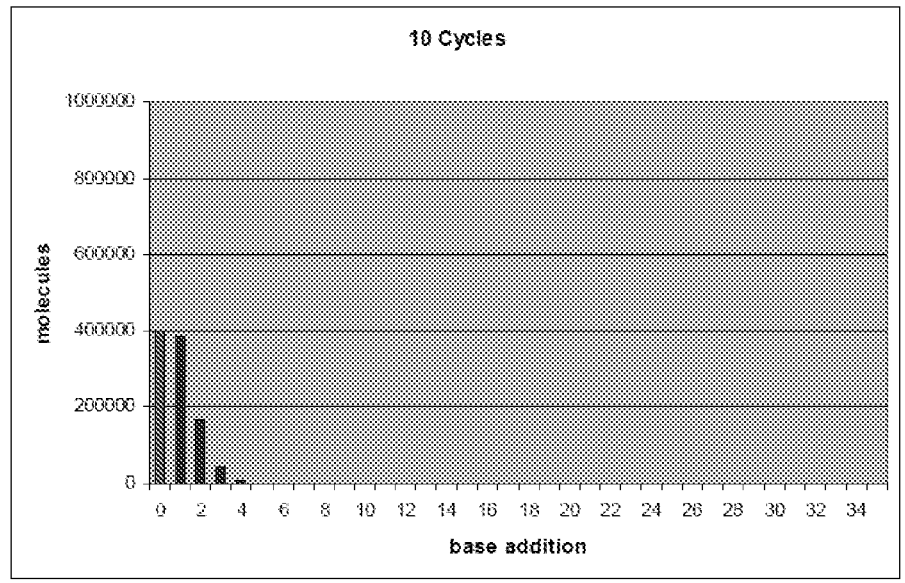
Figure 8:
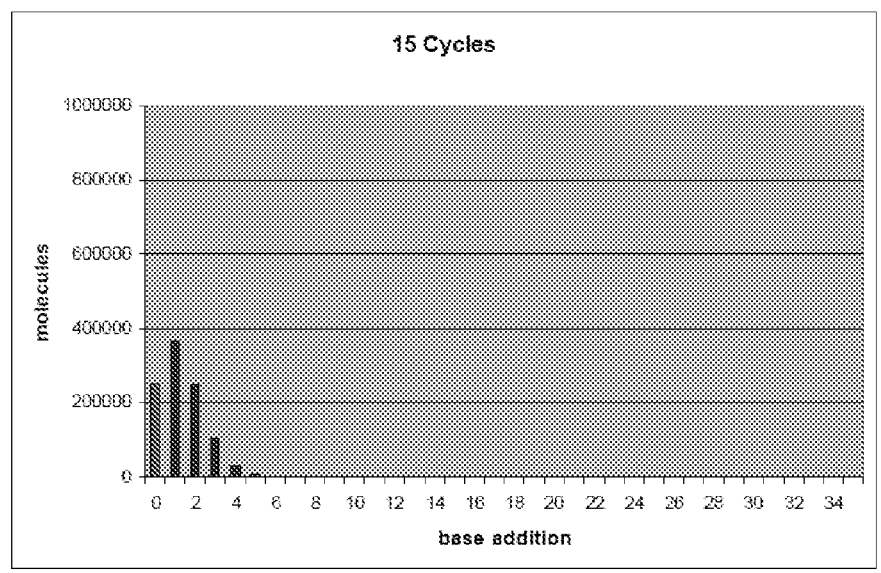
Figure 8:
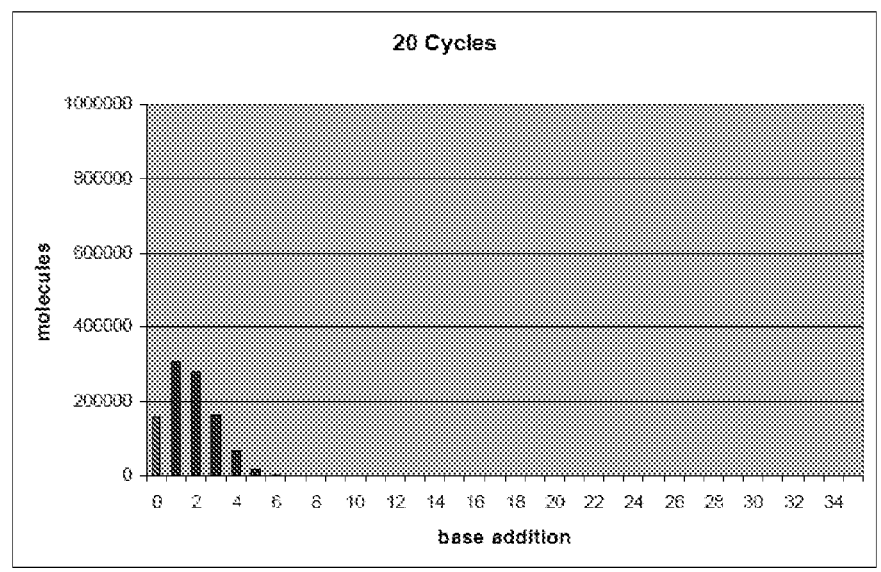
Figure 8:
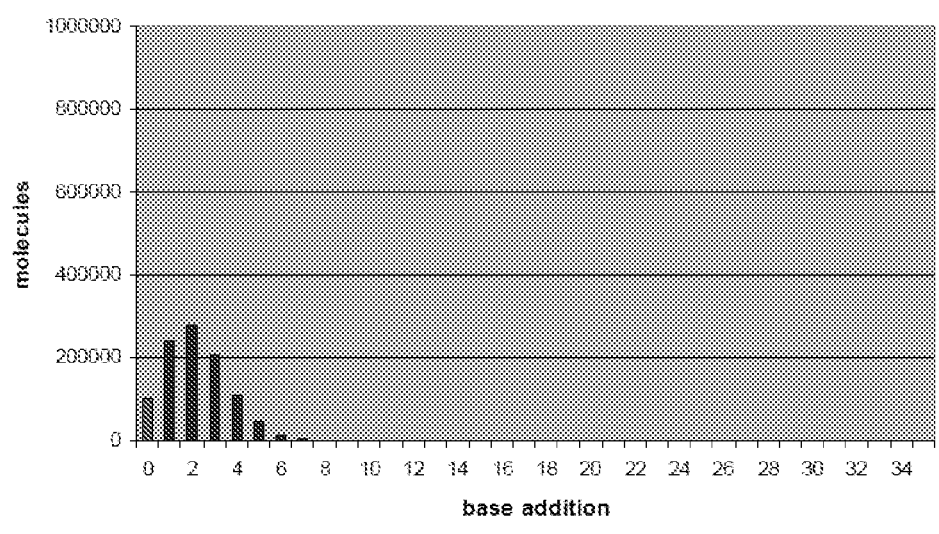
Figure 8:
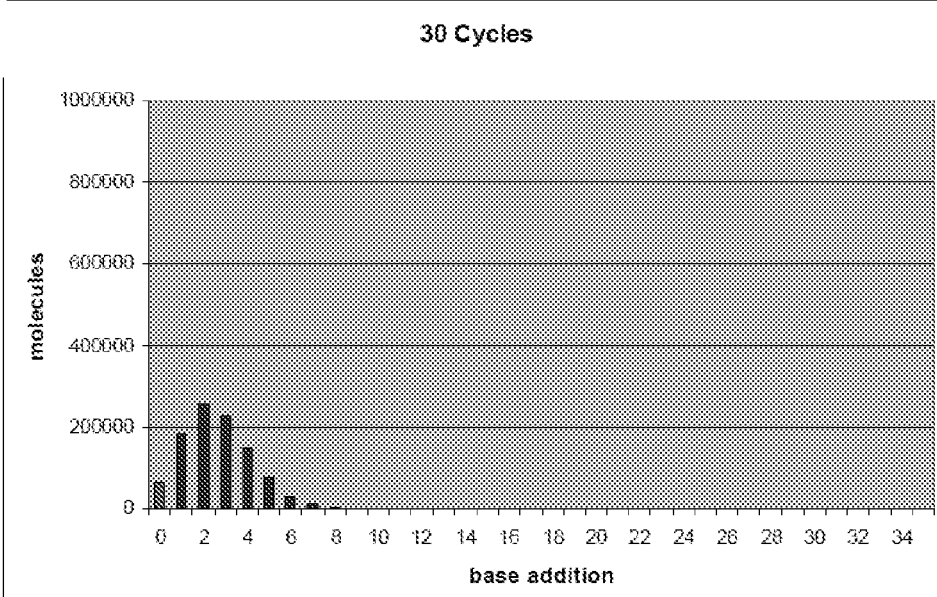
Figure 8:
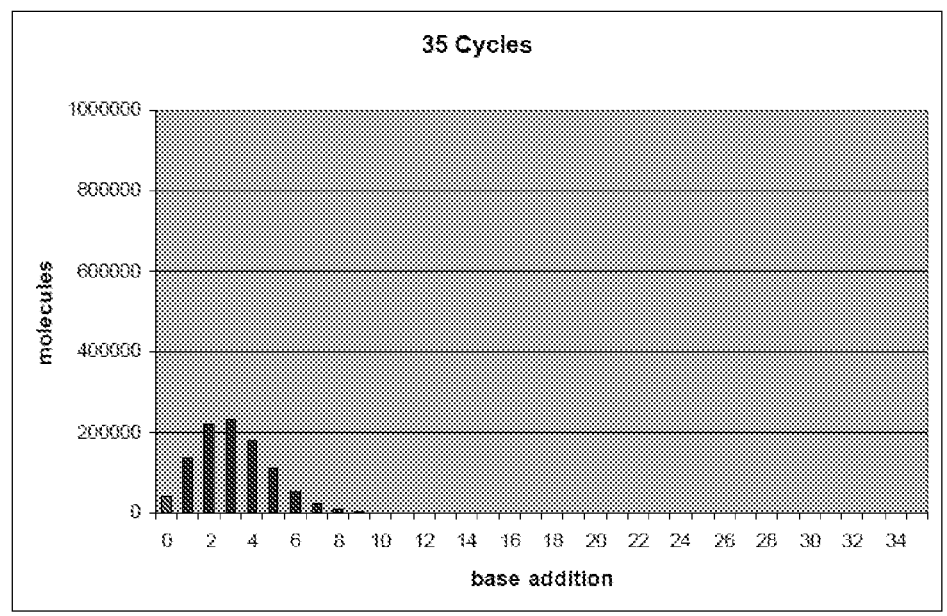
Figure 9:
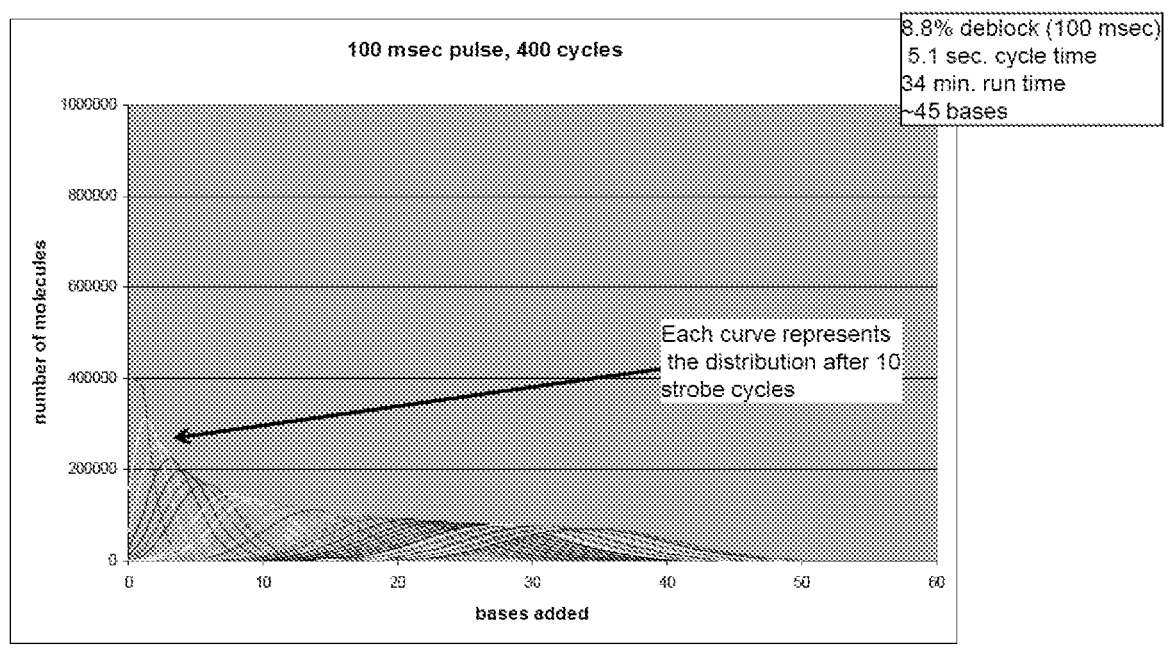
FIG. 9 shows the results of extending cycle number out to 400 cycles (still using 100 mSec strobes of deblocking light), where each curve represents the distribution after 10 strobe cycles.
Figure 10:
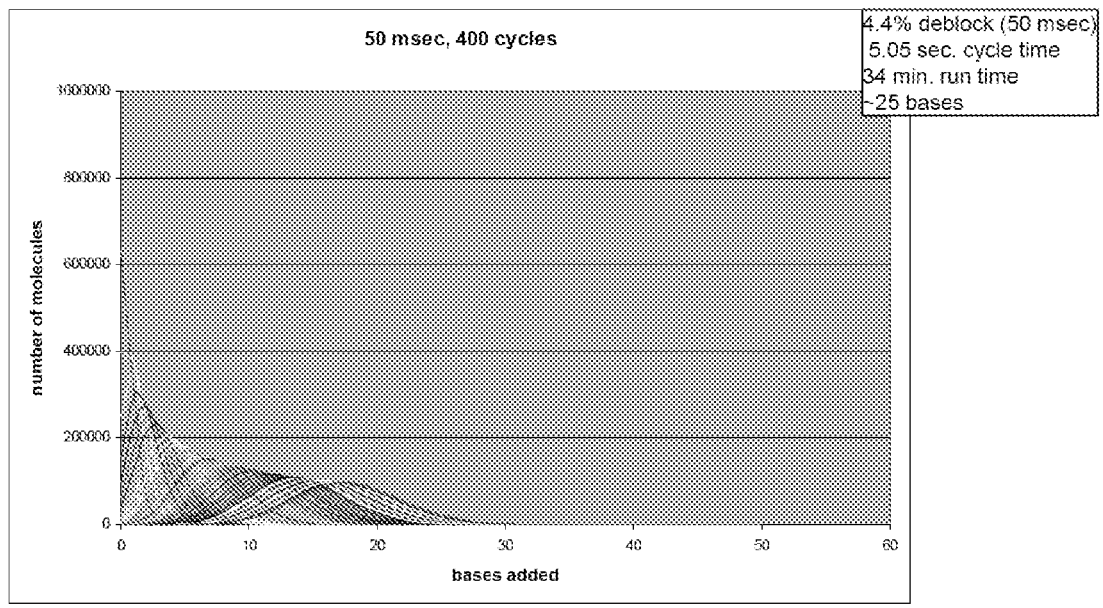
FIG. 10 shows the results of extending the cycle number out to 400 cycles using 50 mSec strobes, where 4.4% of available photolabile bases are deblocked.
Figure 11:
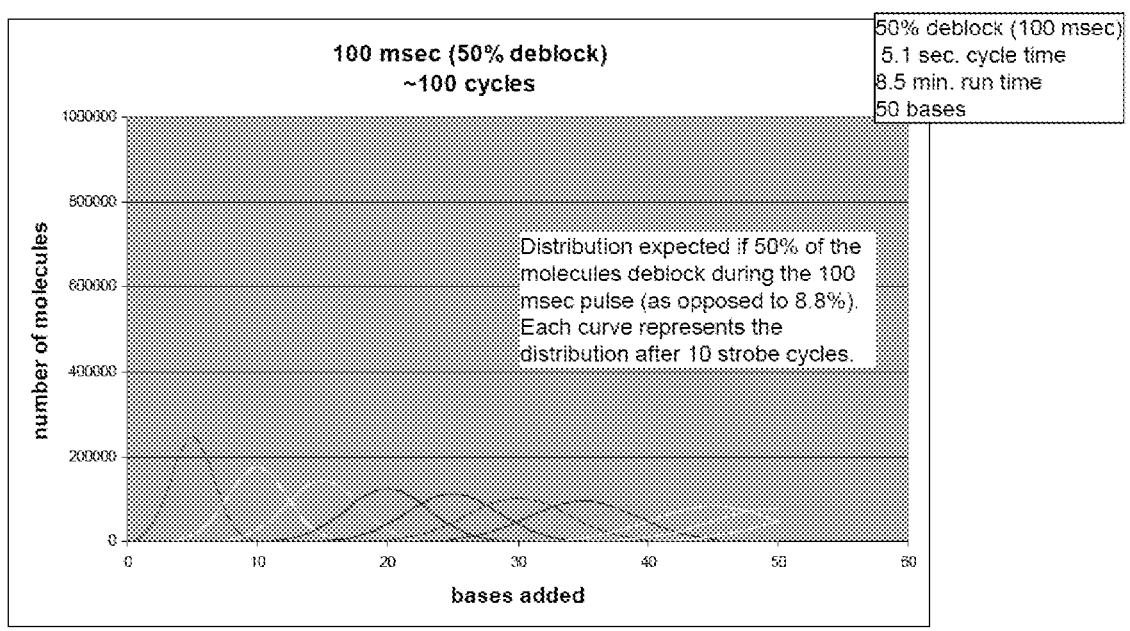
FIG. 11 shows the distribution expected if 50% of the molecules deblock during the 100 msec pulse (as opposed to 8.8%). Each curve represents the distribution after 10 strobe cycles.

FIG. 8 (*a-i*) models 35 strobe cycles starting off with $10^6$ target molecules on the surface. FIG. 8a models cycle 0, where there are $10^6$ molecules on the surface waiting to be deblocked. At cycle 1 (shown in FIG. 8b), 8.8% of the $10^6$ molecules on the surface are deprotected and extended (darker/blue bar), while 91.2% remain blocked (lighter bar). FIG. 8c shows 5 cycles, FIG. 8d shows 10 cycles, FIG. 8e shows 15 cycles, and FIG. 8f shows 20 cycles. FIG. 8f shows that a normal distribution is starting to appear. As shown in FIG. 8g (25 cycles), the distribution curve is slowly moving to the right, while the distribution itself is slowly diminishing and becoming more spread out, with each successive cycle. FIG. 8h shows the distribution after 30 cycles. As shown in FIG. 8i (35 cycles), the normal distribution continues to diminish and spread out, much like Poisson distribution at high copy number. The 35 cycles in FIG. 8i represents about 3 minutes of sequencing run time. FIG. 9 shows the results of extending cycle number out to 400 cycles (still using 100 mSec strobes of deblocking light), where each curve represents the distribution after 10 strobe cycles. FIG. 10 shows the results of extending the cycle number out to 400 cycles using 50 mSec strobes, where 4.4% of available photolabile bases are deblocked. FIG. 11 shows the distribution expected if 50% of the molecules deblock during the 100 msec pulse (as opposed to 8.8%). Each curve represents the distribution after 10 strobe cycles.

The use of short pulses of deprotecting light is beneficially used to detect homopolymers. The capability to detect homopolymers depends on the ability to detect small changes in statistical sampling. Homopolymers reduce the number of base changes during each detection step. A mathematical model for detecting homopolymers is shown in FIG. 12.

Although the invention has been described in connection with specific preferred embodiments, it should be understood that the invention as claimed should not be unduly limited to such specific embodiments. Various modification and variation of the described methods and compositions of the invention will be apparent to those skilled in the art without departing from the scope and spirit of the invention. Indeed, various modifications of the described modes for carrying out the invention understood by those skilled in the relevant fields are intended to be within the scope of the following claims. All publications and patents mentioned in the present application are herein incorporated by reference.

What is claimed is:

1. A system for photocleaving and scanning nucleotide analogs comprising:
   a) a substrate comprising a plurality of wells which each contain a reaction mixture comprising a template nucleic acid, a polymerase, a primer hybridized to said template, and a first nucleotide analog,
   wherein said primer comprises a 3' terminal nucleotide analog with a photolabile blocking group that terminates chain extension, and
   wherein said first nucleotide analog comprises: i) a first detectable moiety, and ii) a photolabile blocking group that terminates chain extension; and
   b) a light system component comprising:
      i) a light source in optical communication with said plurality of wells which provides: A) photocleaving light input that cleaves said photolabile blocking group when it is part of said primer; and B) scanning input light that produces an optical signal from said first detectable moiety after said first nucleotide analog is added to said primer by said polymerase; and
      ii) a light control component comprising a computer processor and a computer program wherein said computer program activates said light source such that a plurality of deblock-scan cycles are generated,
   wherein each of said deblock-scan cycles comprise an initial deblock time period wherein at least a part of said photocleaving light input is passed into said plurality of wells, and a following scan time period wherein at least part of said scanning light input is passed into said plurality of wells, and
   wherein at least one of the following occurs in each of said deblock-scan cycles:
      A) said deblock time period is shorter than said scan time period;
      B) said deblock time period is only long enough to deblock said photolabile blocking groups that are part of said primer in less than all of said plurality of wells; and
      C) said deblock time period is between 25 and 150 mSec and said scan time is at least 200 mSec.

2. The system of claim 1, further comprising c) a detector component in optical communication with said plurality of wells which detects said optical signal from said plurality of wells.

3. The system of claim 1, wherein said substrate is composed of a material selected from the group consisting of: transparent glass, transparent plastic, silicon-titanium oxide, titanium oxide, tantalum oxide, niobium oxide, hafnium oxide, aluminum oxide, zirconium oxide, silicon nitride, aluminum nitride, titanium nitride, polycarbonate (PC), PMMA, and Su8.

4. The system of claim 1, wherein said plurality of optical sensing wells are sized to provide an internal waveguide.

5. The system of claim 4, wherein each of said wells comprises a zero-mode waveguide.

6. The system of claim 1, further comprising an external waveguide.

7. The system of claim 1, wherein said wells are optically coupled to an external waveguide.

8. The system of claim 1, wherein said template nucleic acid in each of said plurality of optical sensing wells is part of a sequencing library.

9. The system of claim 1, wherein said photolabile blocking group that is part of said primer is the same as the photolabile blocking group that is part of said first nucleotide analog.

10. The system of claim 1, wherein said photolabile blocking group that is part of said primer is different from the photolabile blocking group that is part of said first nucleotide analog.

11. The system of claim 1, wherein said photolabile blocking group is selected from the group consisting of: an o-nitrobenzyl blocking group, nitroveratryl, 1-pyrenylmethyl, 6-nitroveratryloxycarbonyl, dimethyldimethoxybenzyloxycarbonyl, 2-nitrobenzyloxycarbonyl, methyl-6-nitropiperonyloxycarbonyl, dimethoxybenzyloxy carbonyl, 5-bromo-7-nitroindolinyl, o-hydroxy-alpha-methyl cinnamoyl, and 2-oxymethylene anthriquinone.

12. The system of claim 1, wherein said light source comprises a first light generating component configured to generate said photocleaving light input, and a second light generating component configured to generate said scanning light input.

13. The system of claim 1, wherein said plurality of wells are optically coupled to an external waveguide, wherein said external waveguide is either one waveguide in optical communication with all of said plurality of wells, or wherein said external waveguide is a plurality of waveguides, one for each of said plurality of wells.

14. A method for photocleaving and detecting nucleotide analogs using a system comprising:
   i) a substrate comprising a plurality of wells, wherein each well contains a reaction mixture comprising a template nucleic acid, a polymerase, a primer hybridized to said template, and a first nucleotide analog,
   wherein said primer comprises a 3' terminal nucleotide analog with a photolabile blocking group that terminates chain extension, and
   wherein said first nucleotide analog comprises: i) a first detectable moiety, and ii) a photolabile blocking group that terminates chain extension; and
   ii) a light system component comprising:
      A) a light source in optical communication with said plurality of wells, wherein said light source provides:
         I) photocleaving light input; and
         II) scanning light input; and
      B) a light control component comprising a computer processor and a computer program wherein said computer program activates said light source such that a plurality of deblock-scan cycles are generated,
      wherein each of said deblock-scan cycles comprises an initial deblock time period wherein at least a portion of said photocleaving light input is passed into said wells, and a following scan time period wherein at least a portion of said scanning light input is passed into said wells, and iii) a detector component in optical communication with said plurality of optical sensing wells, wherein the method comprises:

a) activating said light control component such that said light source provides a plurality of said deblock-scan cycles which deblock said photolabile blocking groups, when said photolabile groups are part of said primer, in at least some of said wells and generates an optical signal from said detectable moiety in said plurality of wells after said first nucleotide analog is added to said primer by said polymerase, wherein at least one of the following occurs in each of said deblock-scan cycles:

A) said deblock time period is shorter than said scan time period;

B) said deblock time period is only long enough to deblock said photolabile blocking groups that are part of said primer in less than all of said plurality of wells; and C) said deblock time period is between 25 and 150 mSec and said scan time is at least 200 mSec; and b) detecting said optical signal from detectable moiety generated during each of said plurality of deblock-scan cycles in said plurality of wells with said detector component.

15. A method for photocleaving and detecting nucleotide analogs using a system comprising:

i) a substrate comprising a plurality of optical sensing wells, wherein each of said optical sensing wells is sized to provide an internal waveguide and/or is optically coupled to an external waveguide, wherein each optical sensing well contains a reaction mixture comprising a template nucleic acid, a polymerase, a primer hybridized to said template, and a first nucleotide analog, wherein said primer comprises a 3' terminal nucleotide analog with a photolabile blocking group that terminates chain extension, and wherein said first nucleotide analog comprises: i) a first detectable moiety, and ii) a photolabile blocking group that terminates chain extension; and ii) a light system component comprising:

A) a light source in optical communication with said internal and/or external waveguides, wherein said light source provides: I) photocleaving light input that generates a first electromagnetic wave in said optical sensing wells when passed into said internal or external waveguides; and II) scanning input light that generates a second electromagnetic wave in said optical sensing wells when passed into said internal or external waveguides; and B) a light control component comprising a computer processor and a computer program wherein said computer program activates said light source such that a plurality of deblock-scan cycles are generated, wherein each of said deblock-scan cycles comprises an initial deblock time period wherein said photocleaving light input is passed into said internal and/or external waveguides, and a following scan time period wherein said scanning light input is passed into said internal and/or external waveguides, and iii) a detector component in optical communication with said plurality of optical sensing wells;

wherein the method comprises:

a) activating said light control component such that said light source provides a plurality of said deblock-scan cycles which deblock said photolabile blocking groups, when they are part of said primer, in at least some of said optical sensing wells and generates an optical signal from said detectable moiety in said plurality of optical sensing wells after said first nucleotide analog is added to said primer by said polymerase, wherein at least one of the following occurs in each of said deblock-scan cycles:

A) said deblock time period is shorter than said scan time period;

B) said deblock time period is only long enough to deblock said photolabile blocking groups that are part of said primer in less than all of said plurality of optical sensing wells; and C) said deblock time period is between 25 and 150 mSec and said scan time is at least 200 mSec; and b) detecting said optical signal from detectable moiety generated during each of said plurality of deblock-scan cycles in said plurality of optical sensing wells with said detector component.

16. The method of claim 15, wherein said detecting provides sequence information for at least a portion of said template nucleic acid in at least some of said plurality of optical sensing wells.

* * * * *